United States Patent [19]

Baumbach et al.

[11] Patent Number: 5,786,458

[45] Date of Patent: Jul. 28, 1998

[54] SELECTIVE STABILIZATION OF PROTEIN DURING VIRAL INACTIVATION

[75] Inventors: George A. Baumbach, Knightdale; David J. Hammond; John M. Lang, both of Raleigh; Cynthia J. Galloway, Garner, all of N.C.

[73] Assignee: Bayer Corporation, Berkeley, Calif.

[21] Appl. No.: 672,255

[22] Filed: Jun. 28, 1996

[51] Int. Cl.$^6$ ..................................................... C07K 3/00
[52] U.S. Cl. ...................... 530/412; 530/413; 530/380; 530/381; 530/329; 210/656
[58] Field of Search .................... 530/412, 413, 530/380, 381, 329; 210/656

[56] References Cited

U.S. PATENT DOCUMENTS 4,673,733   6/1987   Chandra et al. .................... 530/344
4,831,012   5/1989   Estep .................................... 514/6

*Primary Examiner*—Cecilia J. Tsang
*Assistant Examiner*—C. Delacroix-Muirheid
*Attorney, Agent, or Firm*—James A. Giblin; Michael J. Beck

[57] ABSTRACT

A process for viral inactivation of a solution containing a biologically active protein, wherein the process comprises the steps of 1) contacting the solution with an immobilized ligand under conditions which allow protein to bind to the ligand, 2) subjecting the bound protein to a viral inactivation method under conditions which would result in substantial denaturation of the protein if it were not bound to the ligand, and 3) recovering the protein by washing the immobilized protein under conditions which favor the release of the protein into the solution under conditions in which the recovered protein retains its biological activity.

10 Claims, 1 Drawing Sheet

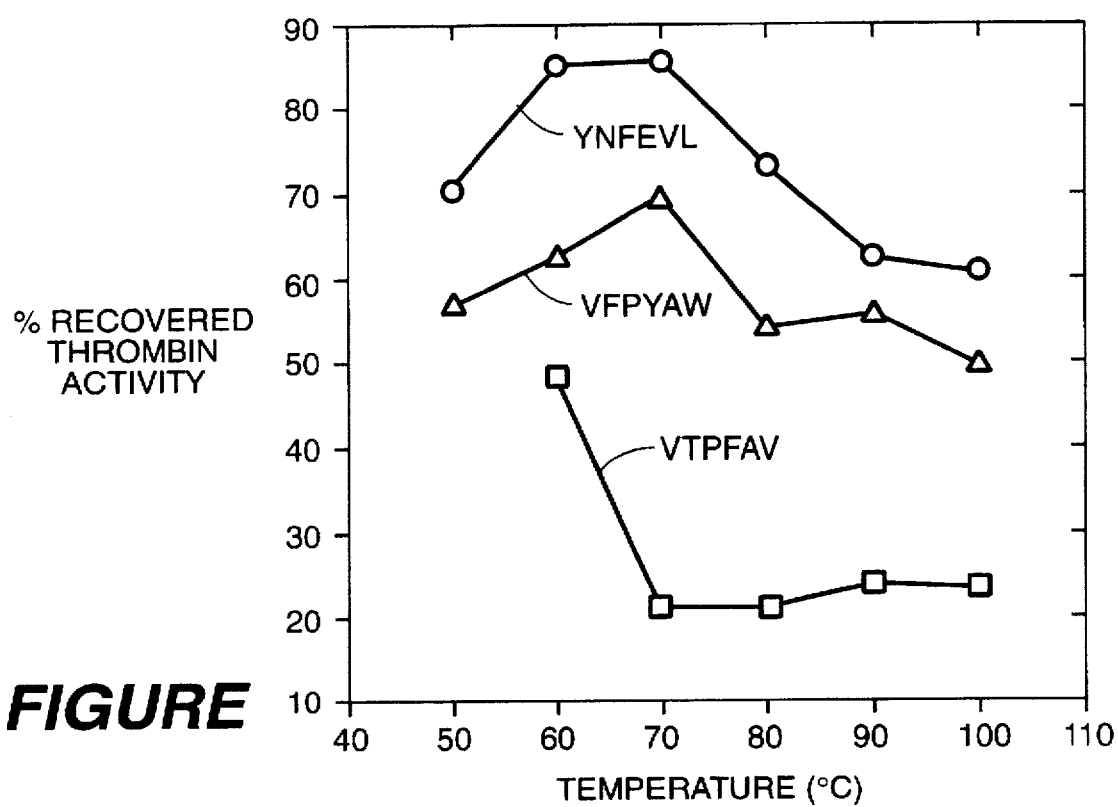
FIGURE

SELECTIVE STABILIZATION OF PROTEIN DURING VIRAL INACTIVATION

BACKGROUND OF THE INVENTION

1. Field

The invention relates generally to viral inactivation of proteins of therapeutic use. Specifically, the invention is a viral inactivation method in which the protein of interest (product) is stabilized by being bound to an affinity resin during the viral inactivation method and may be further purified by selective elution from the column.

2. Background

Biological products derived from human plasma, such as intravenous gamma globulin and Factor VIII, have the potential to transmit human infectious viruses to recipients. There are three levels of control incorporated into the production of the products, to minimize the potential infection of patients using these drugs. The first is to minimize viral load by screening of human source plasma. The second is to ensure that the processes used to manufacture the product from source plasma substantially remove any potential virus from the final product. The third level of control is to incorporate specific viral inactivation methods into the process for production of the product.

Treatment of proteins with a mixture of solvent and detergent is widely used to prevent transmission of enveloped viruses by proteins derived from either biological or biotech sources (Neurath et al., 1985; Piet et al., 1990). This treatment is effective against those viruses which have a lipid-enveloped membrane, and is much less effective against those viruses which do not contain this structure. In recent years, transmission of at least two non-enveloped viruses by the use of a solvent/detergent treated biological product have been described. Hepatitis A virus, a non-enveloped RNA virus, was transmitted to patients using a Factor VIII product which had been treated with solvent detergent (Purcell et al, 1994). Factor VIII has also been implicated in the transmission of a non-enveloped parvovirus, B19, to humans (Lefrere et al, 1994). Clearly, viral inactivation methods with a broader spectrum of anti-viral activity are needed to maintain and improve the safety of biological products.

Treatment of proteins with heat, either as dry powders (Rubinstein, 1984; Thomas, 1985) or in an aqueous solution (Schwinn et al., 1981; Fukushima et al., 1982), has been used to extend the spectrum of anti-viral activity to include non-enveloped viruses. However, inactivation of non-enveloped viruses is generally more difficult than enveloped viruses and often requires longer treatment times or higher temperatures to assure complete inactivation. B19 was transmitted to patients by a Factor VIII product which was dry heat treated at 100° C. for 30 min (Santagostino et al., 1994). Solution pasteurization of FVIII, 10 hours at 63° C., was not sufficient to completely inactivate some non-enveloped viruses (Biesert et al., 1995). In addition to being relatively inefficient for non-enveloped virus inactivation, heating methods also have a tendency to denature the protein product. Despite the addition of small molecule stabilizers, dry heat treatment of intravenous gamma globulin was shown to cause aggregation and loss of potency (Matejtschuk et al., 1995). Solution pasteurization in sorbitol was also shown to cause aggregation of intravenous gamma globulin (Gonzalez et al., 1995). Moreover, non-specific stabilizers such as sugars may also stabilize the viral structure during inactivation. To make heat-based methods of viral inactivation efficient, new methods of stabilizing protein products during heat treatment need to be developed.

Ligand binding to a protein has been shown to increase the thermal stability of the protein in many cases. The binding of 3'GMP to barnase increases the denaturation temperature by about 10° C. (Martinez et al., 1994). The immunosuppressive agent FK520 shifts the unfolding temperature of its binding protein from 68° C. to 83° C. (Marquis-Omer et al., 1991). Binding of heparin to bFGF causes a 31° C. shift, from 59° C. to 90° C., in the temperature required to unfold the protein (Vemuri et al., 1994). These sometimes dramatic ligand-induced increases in the thermal stability of proteins are thought to be related to the energetics of the protein-ligand interaction (Denisov, 1992).

Ligands are often used in the affinity purification of proteins from complex mixtures. For example, heparin coupled to a solid phase is used in the affinity purification of ATIII from human source plasma (Lebing et al., 1994). Immobilized Fv antibody fragments have been used to isolate hen egg lysozyme (Berry et al., 1991). Two methods for purification of fibrinogen from plasma, one by affinity chromatography on ristocetin-agarose (Suzuki et al., 1980) and another by chromatography on protamine-agarose (Dempfle & Heene, 1987), have been reported.

Immobilized small peptide ligands have also been claimed to be generally useful in affinity purification strategies (Baumbach & Hammond, 1992). Kuyas et al. (1990) showed the purification of fibrinogen using a small peptide, GPRPK (SEQ ID NO 1), bound upon a chromatographic support.

Our invention seeks to describe ligands which both bind and stabilize proteins to viral inactivation methods such as heating. By selectively stabilizing a protein to heat by ligand binding, it should be possible to heat the mixture sufficiently to accomplish viral inactivation. Moreover, the ligand can theoretically be re-used many times for both purification and stabilization of the target.

SUMMARY OF THE INVENTION

We have now discovered a novel method of selectively stabilizing a protein of interest in a solution being subjected to a viral inactivation method. Quite surprisingly, we found we could incorporate the viral inactivation method into an affinity purification step, applying viral inactivation conditions which would otherwise result in loss of protein activity. The protein stabilization results from binding to ligands which stabilize the protein to the viral inactivation conditions, thus enabling recovery of a greater percentage of activity. Affinity purification may result from having the ligands immobilized on a substrate such that the protein may selectively bind the ligands and then be eluted from the substrate. We anticipate that combining peptide ligand stabilization and peptide affinity purification will result in more economical commercial production of virally inactivated protein products.

This method is illustrated herein with a peptide affinity column which uses a small peptide segment to bind a protein (thrombin). Thrombin bound on the affinity column is heated to a variety of temperatures for thirty minutes. By binding to the column, thrombin is stabilized and remains active when removed from the column. Without the stabilization provided by the peptide affinity matrix, thrombin is inactivated by heat. Virus added to the column and subjected to heat would not be stabilized because the ligand is specific for only the target protein.

The ligands used in the examples herein are polypeptides, but other types of molecules which have affinity for the protein and which stabilize the protein during viral inactivation may also be used. The ligands may be immobilized by being bound upon various supports, including chromatography supports such as silica and polymer-based resins.

As used herein, biologically active protein means a protein which demonstrates a measurable function or activity or is useful for an intended result (especially as opposed to the same protein in a denatured or useless state). The function, activity, or intended result could be, e.g., an enzymatic activity or a binding affinity. Substantial retention of activity means preferably at least about 50%, more preferably at least about 70%, and most preferably at least about 80% of the activity may be recovered from the process. Substantial denaturation means a loss of at least about 50%, in a worse case at least about 70%, and in an even worse case at least about 80% of the activity of the protein. As a practical matter, it is desirable to recover proteins with as little denaturation as possible. Thus, the process of the current invention may be used where the conditions of the viral inactivation treatment result in a greater amount of activity recovered from the process of the current invention as compared to the amount recovered without using the process of the current invention.

It is believed the invention applies to more methods of viral inactivation of proteins than just heating of the aqueous solution. This process may be applied to various chemical methods for inactivation of viruses which result in denaturation of proteins, with the added benefit that any chemicals used may be removed before eluting the protein from the immobilized ligand. Acid treatment, heating in heptane suspension, chaotropic agents or solvent/detergent, to name a few possibilities, may be incorporated into the current process where protein stability is a problem with the chosen viral inactivation method.

Conditions of viral inactivation may vary depending on the details of the experimental system. It is generally known that, for example, a brief heating at a high temperature may be as effective for inactivating viruses as a longer heating at a somewhat lower temperature. Thus, the time may depend on the net stabilization of the protein bound to the ligand, which will vary from system to system. Optimization of conditions to maximize recovery of active protein with maximal virus clearance is considered to be within the capability of those skilled in the art.

Virus clearance is typically measured by spiking a solution with a known quantity of a model virus, performing a viral inactivation process, and measuring the quantity of active virus in the resulting solution. One $log_{10}$ unit of virus reduction is defined as a lowering of active virus titer by a factor of ten. Substantial viral clearance means preferably at least about three $log_{10}$ units, more preferably at least about four $log_{10}$ units, and most preferably at least about five $log_{10}$ units. Substantially free of virus means having been treated by a virus inactivation method resulting in substantial viral clearance.

BRIEF DESCRIPTION OF THE FIGURE

The FIGURE shows the stabilization of thrombin to heat in the presence of three different peptide affinity resins.

SPECIFIC EMBODIMENTS

BINDING EXPERIMENTS

The peptides VFPYAW, YNFEVL, and VTPFAV (SEQ ID NOS 2, 3, and 4, respectively) were synthesized directly on a solid phase resin (Buettner et al., 1996). Jacketed chromatography columns were loaded with 1 ml of resin each. Water from a controlled temperature water bath was circulated through the column jackets to maintain the temperature at 25° C. Thrombin (200 µg) (Enzyme Research Labs) was loaded on the column in 1 ml of 10 mM Hepes, 1 mM EGTA, 0.1 M NaCl, 0.1% Tween-20 at pH 6.8 (Buffer A). Unbound material was removed from the column by washing with 5 ml of Buffer A, 5 ml of 1M NaCl in Buffer A, 5 ml of 3M NaCl in Buffer A, and finally 5 ml of Buffer A. Thrombin was eluted with 5 ml of 2% acetic acid and collected in tubes containing 1 ml Tris buffer for neutralization. Thrombin activity in samples was assayed according to Axelson et al. (1976), using H-D-Phenylalanyl-L-pipecolyl-L-arginine-p-nitroaniline dihydrochloride (S-2238, Chromogenix, Sweden) as a substrate.

TABLE

| Binding of thrombin to peptide affinity resins. | | | |
|---|---|---|---|
| PEPTIDE (SEQ ID NO) | VFPYAW (2) µg/ml thrombin | YNFEVL (3) µg/ml thrombin | VTPFAV (4) µg/ml thrombin |
| Load | 221.4 | 221.4 | 221.4 |
| wash | 0.8 | 58.7 | 183.4 |
| 1M NaCl | 57.8 | 84.0 | 6.8 |
| 3M NaCl | 23.0 | 20.8 | 0.4 |
| wash | 17.2 | 15.1 | 0.4 |
| elution | 200.9 | 101.3 | 2.5 |

As shown in the Table, the peptide VFPYAW bound 91% of thrombin loaded onto the column. Peptide YNFEVL bound thrombin less tightly, with only 46% remaining after the salt washes. Peptide VTPFAV was included as a "negative" control. It did not bind thrombin, with only residual (2.5%) thrombin remaining after the salt washes.

STABILIZATION EXPERIMENTS

Three columns, each containing one of the peptide affinity resins, were equilibrated to the indicated temperatures (see the FIGURE) by circulation of water through the column jackets for 30 minutes. Then 200 µg of thrombin was loaded onto the resins as before; however, no attempt to remove thrombin from the resin with salt washes was performed. After 30 minutes at the desired temperature, 1 ml of 2% acetic acid was added to elute thrombin from the column, and samples were collected into Tris buffer as before.

As shown in the FIGURE, at 70° C. thrombin was inactivated to baseline levels when applied to the non-binding resin. However, when thrombin was applied to resin VFPYAW (SEQ ID NO 2), nearly 70% of thrombin activity was retained at 70° C. Resin YNFEVL (SEQ ID NO 3), the more weakly binding resin, retained 85% of protein activity at 70° C. Above 70° C., the retention of thrombin activity declined, but remained higher on the binding resins than the non-binding resin.

CONCLUSION

We have shown that by binding a protein in solution to a peptide affinity resin, we can substantially increase the stability of a protein to heating. In particular, 80% of thrombin activity was recovered from the YNFEVL-resin (SEQ ID NO 3) and about 70% was recovered from the VFPYAW-resin (SEQ ID NO 2) after heating at 70° C. for 30 minutes, conditions which otherwise result in denaturation of the protein. Because temperatures of 60° C. and above are often used to inactivate viruses which could contaminate products derived from human plasma, this new technique should make it possible to treat proteins with heat without substantial denaturation of the protein. This technique thus forms the basis of a specific viral inactivation step which can be incorporated into the production process of many protein products. Because the protein product to be treated is bound specifically to a peptide affinity resin, this technique may also result in the ability to both virally inactivate and affinity purify a protein product in the same production step. Such a method would result in economies of scale and efficiency in the production of proteins for therapeutic use, and result in benefits in the manufacturing process.

The above examples are intended to illustrate the invention and it is thought variations will occur to those skilled in the art. Accordingly, it is intended that the scope of the invention should be limited only by the claims below.

REFERENCES

Axelson G., et al., Prothrombin determination by means of chromogenic peptide substrate, Thromb Haemost 36: 517 (1976).

Baumbach, G. A. and D. H. Hammond, Protein purification using affinity ligands deduced from peptide libraries, Biopharm 5: 24–35 (1992).

Berry, M. J., et al., Immobilization of Fv antibody fragments on porous silica and their utility in affinity chromatography, J. Chromatog. 587: 161–169 (1991).

Biesert, L., et al., Virus validation experiments on the production process of OCTAVI SDPlus, Blood Coagul. Fibrinolysis 6(Suppl 2): S48–54 (1995).

Buettner, J. A., et al., Chemically derived peptide libraries: a new resin and methodology for lead identification, Int. J. Peptide Res 47: 70–83 (1996).

Dempfle, C. E. & D. L. Heene, Purification of human fibrinogen by chromatography on protamine-agarose, Thromb. Res. 46: 19–27 (1987).

Denisov, I. G., Thermal stability of proteins in intermolecular complexes, Biophys. Chem. (Neth.) 44: 71–75 (1992).

Fukushima, T., et al., Process for heat treatment of aqueous solution containing human blood coagulation factor VIII:, U.S. Pat. No. 4,327,086 (Apr. 27, 1982).

Gonzalez, M., et al., Thermal stability of human immunoglobulins with sorbitol, Vox Sang. 68: 1–4 (1995).

Kuyas, C., et al., Isolation of human fibrinogen and its derivatives by affinity chromatography on Gly-Pro-Arg-Pro-Lys-Fractogel, Thromb. Haemost. 63: 439–444 (1990).

Lebing, W. R., et al., A highly purified antithrombin III concentrate prepared from human plasma fraction IV-1 by affinity chromatography, Vox Sang 67: 117–124 (1994).

Lefrere, J. J., et al., B19 parvovirus DNA in solvent/detergent-treated anti-haemophilia concentrates, Lancet 343: 211–12 (1994).

Martinez, J. C., et al., A calorimetric study of the thermal stability of barnase and its interaction with 3 GMP, Biochemistry 33: 3919–3926 (1994).

Marquis-Omer, D., et al., Stabilization of the FK506 binding protein by ligand binding, Biochem. Biophys. Res. Comm. 179: 741–748 (1991).

Matejtschuk, P., et al., Dry heat treatment of intravenous immunoglobulin - some practical considerations, Vox Sang. 68: 255–257 (1995).

Neurath, A. R., & B. Horowitz, Undenatured virus-free biologically active protein derivatives, U.S. Pat. No. 4,540,573 (Sep. 10, 1985).

Piet, M. P. J., et al., The use of tri(n-butyl)phosphate detergent mixtures to inactivate hepatitis viruses and human immunodeficiency virus in plasma and plasma's subsequent fractionation, Transfusion 30: 592–98 (1990).

Purcell, R. H., et al., Virology of the Hepatitis A epidemic in Italy, Vox Sang. 67(supp. 4): 2–7 (1994).

Rubinstein, A., Heat treatment of lyophilized blood clotting factor VIII concentrate, U.S. Pat. No. 4,456,590 (Jun. 26, 1984).

Santagostino, E., et al., Eliminating parvovirus B19 from blood products, Lancet 343: 798 (1994).

Schwinn, H., et al., Blood coagulation factors and process for their manufacture, U.S. Pat. No. 4,297,344 (Oct. 27, 1981).

Suzuki, K., et al., A simple technique for purification of fibrinogen from plasma by affinity chromatography on ristocetin-agarose, Thromb. Res. 18: 707–715 (1980).

Thomas, W. R., Process for making novel blood clotting enzyme compositions, U.S. Pat. No. 4,495,278 (Jan. 22, 1985).

Vemuri, S., et al., The stability of bFGF against thermal denaturation, J. Pharm. Pharmacol. 46: 481–486 (1994).

---

What is claimed is:

1. A process for inactivating virus which may be present in an aqueous solution containing a free biologically active protein, wherein the process comprises the steps of
   a) contacting the solution with an immobilized polypeptide which binds to the protein and which stabilizes the protein during viral inactivation, said contacting being done under conditions which allow protein to bind to the polypeptide, thereby resulting in a bound protein,
   b) subjecting the bound protein to a viral inactivation treatment under conditions which result in less denaturation of the protein than if the treatment were performed on the free protein in solution, and
   c) eluting the protein by washing, the bound protein of step b) under conditions which favor the release of protein into solution and under conditions in which the recovered protein substantially retains its biological activity.

2. The process of claim 1, further comprising a wash step between steps a) and b) and a wash step between steps b) and c), said wash steps being performed under conditions which selectively elute impurities and which result in the protein recovered in step c) having increased purity.

3. The process of claim 1 wherein the protein recovered in step c) is substantially free of non-enveloped virus.

4. The process of claim 1 wherein the protein recovered in step c) is substantially free of enveloped virus.

5. The process of claim 1 wherein the protein is thrombin.

6. The process of claim 1 wherein the ligand is immobilized by being covalently bound to a chromatographic support.

7. The process of claim 1 wherein the viral inactivation method is heating to at least 60° C. for a period of time and under conditions which result in substantial viral clearance.

8. The process of claim 7 wherein the viral inactivation method is heating to at least 70° C. for a period of time and under conditions which result in substantial viral clearance.

9. A process for inactivating virus which may be present in an aqueous solution containing thrombin, wherein the process comprises the steps of a) contacting the solution with an immobilized ligand which binds to the thrombin under conditions which allow thrombin to bind to the ligand, thereby resulting in bound thrombin, wherein said immobilized ligand is comprised of a polypeptide having a sequence selected from the group consisting of Val-Phe-Pro-Tyr-Ala-Trp and Tyr-Asn-Phe-Glu-Val-Leu (SEQ ID NOS 2 and 3, respectively), b) subjecting the bound thrombin to a viral inactivation treatment under conditions which result in less denaturation of the thrombin than if the treatment were performed on the free thrombin in solution, and c) eluting the thrombin by washing the bound thrombin of step b) under conditions which favor the release of thrombin into solution and under conditions in which the recovered thrombin substantially retains its biological activity.

10. The process of claim 9 wherein the polypeptide is covalently bound to a chromatographic support.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide (xi) SEQUENCE DESCRIPTION: SEQ ID NO:1:

Gly Pro Arg Pro Lys
1               5

(2) INFORMATION FOR SEQ ID NO:2:

(i) SEQUENCE CHARACTERISTICS:
       (A) LENGTH: 6
       (B) TYPE: amino acid
       (C) STRANDEDNESS: single strand
       (D) TOPOLOGY: linear (ii) MOLECULE TYPE:
       (A) DESCRIPTION: peptide (xi) SEQUENCE DESCRIPTION: SEQ ID NO:2:

Val Phe Pro Tyr Ala Trp
1               5

(2) INFORMATION FOR SEQ ID NO:3:

(i) SEQUENCE CHARACTERISTICS:
       (A) LENGTH: 6
       (B) TYPE: amino acid
       (C) STRANDEDNESS: single strand
       (D) TOPOLOGY: linear (ii) MOLECULE TYPE:
       (A) DESCRIPTION: peptide (xi) SEQUENCE DESCRIPTION: SEQ ID NO:3:

Tyr Asn Phe Glu Val Leu
1               5

(2) INFORMATION FOR SEQ ID NO:4:

(i) SEQUENCE CHARACTERISTICS:
       (A) LENGTH: 6
       (B) TYPE: amino acid
       (C) STRANDEDNESS: single strand
       (D) TOPOLOGY: linear (ii) MOLECULE TYPE:
       (A) DESCRIPTION: peptide (xi) SEQUENCE DESCRIPTION: SEQ ID NO:4:

Val Thr Pro Phe Ala Val
1               5